United States Patent
Busacker et al.

(10) Patent No.: US 7,561,914 B2
(45) Date of Patent: Jul. 14, 2009

(54) METHOD OF CONTINUOUS CAPTURE VERIFICATION IN CARDIAC RESYNCHRONIZATION DEVICES

(75) Inventors: James W. Busacker, St. Anthony, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 461 days.

(21) Appl. No.: 11/312,102

(22) Filed: Dec. 20, 2005

(65) Prior Publication Data

US 2006/0161207 A1 Jul. 20, 2006

Related U.S. Application Data

(60) Provisional application No. 60/637,571, filed on Dec. 20, 2004, provisional application No. 60/637,532, filed on Dec. 20, 2004, provisional application No. 60/637,633, filed on Dec. 20, 2004, provisional application No. 60/637,620, filed on Dec. 20, 2004.

(51) Int. Cl.
*A61N 1/00* (2006.01)

(52) U.S. Cl. ....................................... 607/28

(58) Field of Classification Search .................. 607/9, 607/27, 28
See application file for complete search history.

(56) References Cited

U.S. PATENT DOCUMENTS

| 4,428,378 | A | | 1/1984 | Anderson et al. | |
|---|---|---|---|---|---|
| 5,052,388 | A | | 10/1991 | Sivula et al. | |
| 6,148,234 | A | * | 11/2000 | Struble | 607/28 |
| 6,456,881 | B1 | * | 9/2002 | Bornzin et al. | 607/27 |
| 6,496,730 | B1 | * | 12/2002 | Kleckner et al. | 607/9 |
| 6,549,806 | B1 | * | 4/2003 | Kroll | 607/27 |
| RE38,119 | E | * | 5/2003 | Mower | 607/9 |
| 6,772,005 | B2 | | 8/2004 | Casavant et al. | |
| 6,871,096 | B2 | | 3/2005 | Hill | |
| 2001/0049542 | A1 | | 12/2001 | Florio et al. | |
| 2001/0049543 | A1 | * | 12/2001 | Kroll | 607/28 |
| 2002/0068959 | A1 | * | 6/2002 | Warren et al. | 607/28 |
| 2002/0143368 | A1 | * | 10/2002 | Bakels et al. | 607/9 |
| 2003/0083700 | A1 | * | 5/2003 | Hill | 607/9 |
| 2003/0083711 | A1 | * | 5/2003 | Yonce et al. | 607/27 |

(Continued)

FOREIGN PATENT DOCUMENTS

EP 1155712 A2 11/2001

(Continued)

*Primary Examiner*—Mark W Bockelman
*Assistant Examiner*—Roland Dinga
(74) *Attorney, Agent, or Firm*—Stephen W. Bauer

(57) ABSTRACT

In bi-ventricular pacing devices (including CRT devices) analysis of myocardial electrogram signals in one ventricle (e.g., a left ventricle, or "LV") can be used to infer capture or loss-of-capture (LOC) of an earlier stimulus pulse in the same ventricle, on a continuous (every pacing cycle), triggered, aperiodic and/or periodic basis. Rather than using an evoked-response principle as has been the basis of capture detection in prior art and other systems, a principle employed via the present invention uses evidence of inter-ventricular conduction (i.e., from the opposite chamber) and/or atrio-ventricular conduction as evidence of LOC, since a non-capturing pacing stimulus provided to a first chamber will allow the myocardial tissue of the first chamber to remain non-refractory and thus inter-ventricular and atrio-ventricular wavefront propagation and conduction can commence and be detected thereby revealing whether LOC has occurred.

13 Claims, 4 Drawing Sheets

U.S. PATENT DOCUMENTS

| | | | |
|---|---|---|---|
| 2003/0100925 A1* | 5/2003 | Pape et al. | 607/17 |
| 2003/0195579 A1* | 10/2003 | Bradley et al. | 607/27 |
| 2003/0204214 A1* | 10/2003 | Ferek-Patric | 607/27 |
| 2004/0116971 A1* | 6/2004 | Bjorling et al. | 607/9 |
| 2006/0155338 A1 | 7/2006 | Mongeon et al. | |
| 2006/0161207 A1 | 7/2006 | Busacker et al. | |

FOREIGN PATENT DOCUMENTS

| | | |
|---|---|---|
| EP | 1543864 A | 6/2005 |
| WO | WO03037427 A | 5/2003 |
| WO | WO2005089865 A | 9/2005 |
| WO | WO2006069033 A1 | 6/2006 |

* cited by examiner

METHOD OF CONTINUOUS CAPTURE VERIFICATION IN CARDIAC RESYNCHRONIZATION DEVICES

PRIORITY CLAIM AND CROSS REFERENCE TO RELATED APPLICATIONS

This non-provisional U.S. patent application claims the benefit of the filing of the following four (4) provisional U.S. patent applications each of which was filed on 20 Dec. 2004: a provisional application by Kleckner et al.; namely Ser. No. 60/637,532 entitled, "LV THRESHOLD MEASUREMENT AND CAPTURE MANAGEMENT;" a provisional U.S. patent application by Mongeon et al.; namely Ser. No. 60/637,633 entitled "BI-VENTRICULAR VENTRICULAR CAPTURE MANAGEMENT IN CARDIAC RESYNCRONIZATION THERAPY (CRT) DELIVERY DEVICES;" a provisional U.S. patent application by Sheldon et al.; namely Ser. No. 60/637,571 entitled "METHOD OF CONTINUOUS CAPTURE VERIFICATIONS IN CARDIAC RESYNCHRONIZATION DEVICES;" and a provisional U.S. patent application by Sheth et al., namely Ser. No. 60/637,620 entitled "AUTOMATIC LV/RV CAPTURE VERIFICATION AND DIAGNOSTICS," the contents of the forgoing applications (including all appended exhibits) are hereby incorporated by reference herein.

FIELD OF THE INVENTION

The invention pertains to cardiac pacing systems and relates to apparatus and methods for automatically verifying pacing capture of a ventricular chamber. In particular, the invention relates to verification of pacing capture for both ventricular chambers during a cardiac resynchronization therapy (CRT) delivery, such as a bi-ventricular pacing therapy or unidirectional fusion-type CRT delivery.

BACKGROUND OF THE INVENTION

Cardiac resynchronization cardiac pacing devices operate by either delivering pacing stimulus to both ventricles or to one ventricle with the desired result of a more or less simultaneous mechanical contraction and ejection of blood from the ventricles. However, due to a number of factors for a variety of patients such cardiac pacing systems may not always effectively delivery CRT. For example, varying capture thresholds, pacing lead and/or electrode migration or dislodgement, time required for appropriate signal processing, confounding conduction delays or conduction blockages, diverse electrode placement locations, and the like.

In either form of CRT delivery, whether fusion-based or the more traditional bi-ventricular stimulation, confirming that pacing stimulus captures each paced ventricle is a very important clinical issue so that the desired benefits of the CRT are in fact delivered to a patient.

Assuming that the reader is familiar with bi-ventricular pacing, the following should provide additional insight into the importance of capture detection in a fusion-based bi-ventricular pacing engine. One premise underlying fusion-based pacing is the notion that a fusion-based evoked left ventricular (LV) depolarization enhances stroke volume in hearts where the right ventricle (RV) depolarizes first. This is commonly due to intact atrio-ventricular (AV) conduction to the RV of a preceding intrinsic or evoked atrial depolarization wave front, and wherein the AV conducted depolarization of the LV is unduly delayed. The fusion depolarization of the LV is attained by timing the delivery of the LV pace (LVp) pulse to follow the intrinsic depolarization of the RV but to precede the intrinsic depolarization of the LV. Specifically, an RV pace (RVp) pulse is not delivered due to the inhibition of the RVp event upon the sensing of RV depolarization (RVs), allowing natural propagation of the wave front and depolarization of the intraventricular septum, while an LVp pulse is delivered in fusion with the RV depolarization. For supporting mode switches to alternate pacing modalities, fusion-based CRT delivery engines typically include at least one electrode in each ventricle which allows such engines to be used in conjunction with the present invention, as will be apparent upon review of the following written description and drawings of the invention.

Left ventricular capture in particular is a clinical issue with present-generation (and foreseeable) CRT systems, due to acknowledged difficulty of maintaining stable lead situation in the cardiac venous anatomy. Since CRT delivery becomes ineffective (possibly even deleterious) if LV capture is lost, diagnosis of dislodgment and maintenance of capture are high priorities.

Cardiac Resynchronization Therapy (CRT) devices have been shown to improve quality of life (QOL), exercise capacity and New York Heart Association (NYHA) heart failure class. The NYHA rating varies from Class I to Class IV, as follows: Class I: patients with no limitation of activities; they suffer no symptoms from ordinary activities. Class II: patients with slight, mild limitation of activity; they are comfortable with rest or with mild exertion. Class III: patients with marked limitation of activity; they are comfortable only at rest. Class IV: patients who should be at complete rest, confined to bed or chair; any physical activity brings on discomfort and symptoms occur at rest.

Currently approved CRT devices incorporate bi-ventricular pacing technology with simultaneous pacing in the right ventricle (RV) and the left ventricle (LV). Since the devices are implanted for the essentially only to provide continuous bi-ventricular pacing therapy, it is imperative that the each pacing pulse stimulus delivered to the two LV and RV provide an evoked response (i.e., each stimulus delivered to a ventricle "captures" the ventricle). Thus, if electrodes disposed in electrical communication with a ventricle rapidly sense depolarization wavefronts a control sequence for the pacing engine will inhibit ventricular pacing. For example, such a situation occurs during rapidly conducted atrial fibrillation (AF). When bi-ventricular pacing is inhibited the patient's symptoms of heart failure return, and can sometimes even worsen as compared to their pre-implant status. Similarly, if one of the pacing sites loses capture (e.g., the LV) the subsequent RV-only pacing will prevent the patient from receiving the intended benefit of CRT delivery. To that end the inventors have addressed a need in the art regarding capture verification in heart failure devices, such as bi-ventricular CRT devices that indicates when capture is occurring in both the LV and the RV.

Presently, the only somewhat similar diagnostic available in CRT devices is percent-ventricular pacing (% Vpacing), which indicates the percentage of time bi-ventricular pacing therapy is being delivered; however, a limitation of the % Vpacing metric is that bi-ventricular pacing may be "occurring" close to 100% of the time but the LV chamber may not be captured at all. Currently, cardiac device specialists assess LV capture acutely during office visits by looking at the morphology of an electrogram (EGM) or by temporarily setting pacing to RV-only and LV-only pacing. Current state of the art pacemakers (e.g., the Kappa® brand family of pacemakers provided by Medtronic, Inc.) incorporate ventricular capture management algorithms. However, such algorithms require specific circuitry and sensing capabilities to be able to perform this function that are not currently available in the CRT products. Also, the feasibility of this technology for LV capture management has yet to be established. Note that the present invention is primarily intended for ventricular capture verification, and is not directed solely to ventricular capture management, although the benefits of the invention advantageously contribute to both capture verification and capture management, particularly of the left ventricle (LV).

A need therefore exists in the art to effectively chronically deliver ventricular pacing therapies (including CRT) to patients who might not otherwise receive the full benefit of such therapies.

SUMMARY

In bi-ventricular pacing devices (including CRT devices) analysis of myocardial electrogram signals in one ventricle (e.g., a left ventricle, or herein "LV") can be used to infer capture or loss-of-capture (LOC) of an earlier stimulus pulse in the same ventricle, on a continuous (every pacing cycle) or periodic basis. Rather than using an evoked-response principle as has been the basis of capture detection in prior art and other systems, a principle employed by the present invention uses evidence of inter-ventricular conduction (i.e., from the opposite chamber) as evidence of LOC, since a non-capturing pacing stimulus provided to a first chamber will allow the myocardial tissue of the first chamber to remain non-refractory and thus inter-ventricular (or atrio-ventricular) wavefront propagation and conduction will commence. The time interval from delivery of the pacing stimulus to detection of the evoked or intrinsic, inter-ventricular response can be compared to a nominal threshold or a threshold particularly chosen for a given patient. In addition, the time intervals can vary depending on recent or present heart rate, activity sensor output signal(s), pacing mode and the like.

To perform LOC determination for both ventricles during a single cardiac cycle each ventricle receives a pacing stimulus at approximately, or precisely, the same moment. Assuming no so-called blanking period imposed upon any sense amplifiers operatively coupled to each chamber, each captured chamber would more or less instantaneously respond to the locally delivered supra-threshold pacing stimuli. Thus, each chamber would become refractory for a time interval (until repolarization occurs). However, if one or both pacing stimuli is sub-threshold (e.g., too low amplitude and/or pulse width, etc.) a sensed ventricular event occurring in any non-captured chamber will likely occur subsequent (by more than 25 or 50 ms) to the pacing therapy delivery.

Using existing sense amplifiers and associated circuitry, simple and efficient signal analysis, and discrimination of the conducted signal of interest (from unwanted signals of cardiac activity such as T-waves, premature ventricular contractions, or "PVCs," far-field R-waves, and the like) can be enhanced as needed based on the timing the sensed signal, its magnitude or other morphology characteristics, as registered by suitable circuitry.

Ventricular sensing of intrinsic (not evoked) depolarization signal is thus used to infer LOC, as a basis for diagnostic and auto-adjustment of stimulus output, in CRT or multi-site bradycardia therapy device.

The foregoing and other aspects and features of the present invention will be more readily understood from the following detailed description of the embodiments thereof, when considered in conjunction with the drawings, in which like reference numerals indicate similar structures throughout the several views.

DETAILED DESCRIPTION OF THE ILLUSTRATED EMBODIMENTS

In the following detailed description, references are made to illustrative embodiments for carrying out methods of confirming pacing capture of ventricular pacing stimulation. It is understood that other embodiments may be utilized without departing from the scope of the invention. For example, the invention is disclosed in detail herein in the context of a bi-ventricular CRT delivery. In one form of the invention, a bi-ventricular pacing regimen susceptible of continuous capture verification is based on the principle that delivery of pacing stimulus sufficient to capture each ventricle should preclude inter-ventricular conduction due to the fact that each ventricle is refractory following the evoked depolarization Thus, ventricular sensing in a first ventricle (or both ventricles) following pacing stimulus delivery to both ventricles can be used on a beat-to-beat basis or can be invoked as desired to verify pacing capture of said ventricles. Thus, loss-of-capture (LOC) can be declared, verified or managed and one of several possible responses initiated. For example, the pacing pulse stimulus can be adjusted (e.g., modified pulse amplitude, pulse width, polarity, frequency, etc.), a pacing mode-switch can be implemented, and/or in relatively extreme cases a clinician can attempt to adjust the system, including electrode location, to improve pacing capture.

A cardiac pacing apparatus, according to the invention, comprises a programmable implantable pulse generator (IPG) that can be operated as a dual- or triple-chamber pacing system having an AV synchronous operating mode for restoring upper and lower heart chamber synchronization and/or right and left atrial and/or ventricular chamber depolarization synchrony. A system according to the invention efficiently provides cardiac resynchronization therapy (CRT) with a single ventricular stimulus per cardiac cycle in a fusion-inducing CRT delivery or with a pair of synchronized bi-ventricular pacing stimulus per cardiac cycle.

The present invention provides enhanced hemodynamic performance for patients that benefit from CRT delivery due to various forms of heart failure, ventricular dysfunctions and/or ventricular conduction abnormalities. Pacing systems according to the present invention can also include rate responsive features and anti-tachyarrhythmia pacing and the like. In addition, a system according to the invention can include cardioversion and/or defibrillation therapy delivery.

Figure 1:
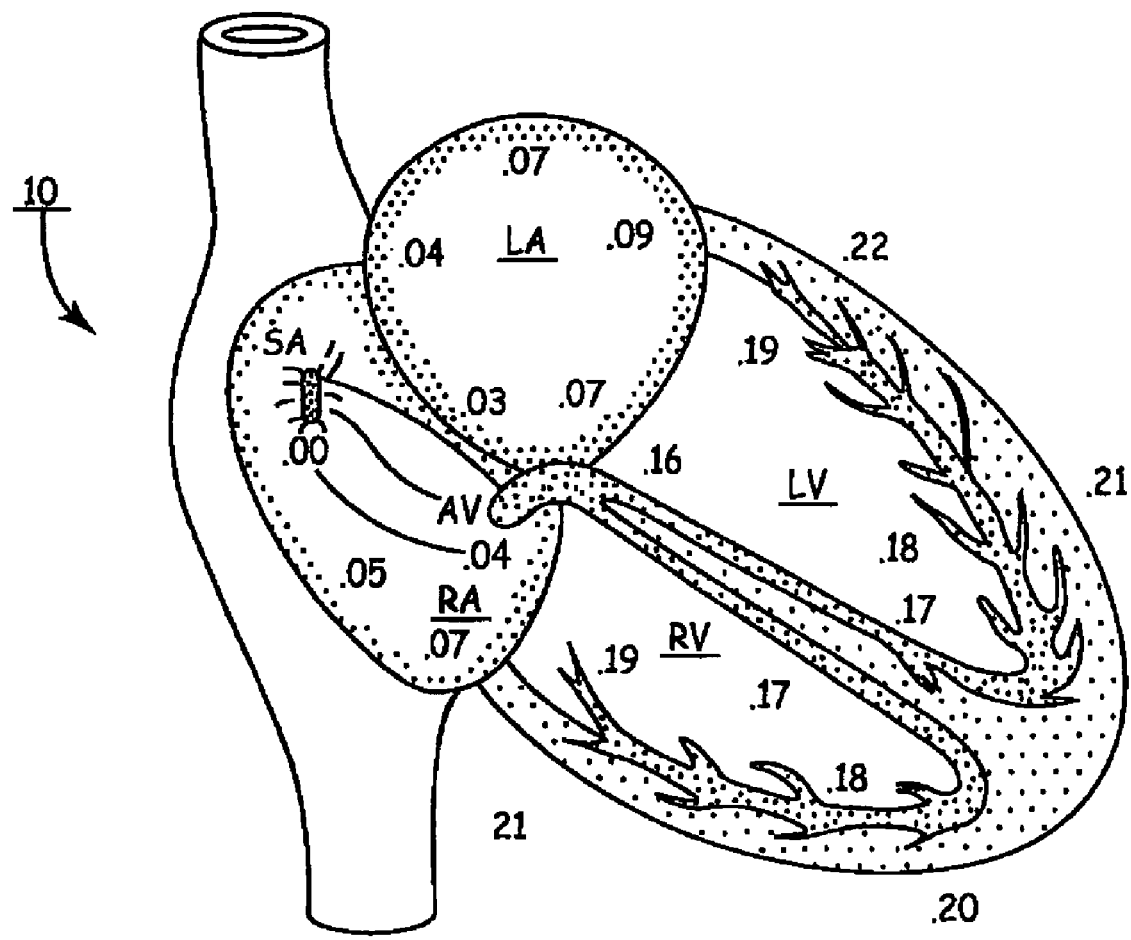
FIG. 1 is an illustration of transmission of a normal cardiac conduction system through which depolarization waves are propagated through the heart in a normal intrinsic electrical activation sequence.

In accordance with an aspect of the present invention, a method and apparatus is provided to mimic the normal depolarization-repolarization cardiac cycle sequence (nominally depicted in FIG. 1) and restore cardiac intra- and/or inter-ventricular synchrony between the RV and LV that contributes to adequate cardiac output related to the synchronized electromechanical performance of the RV and LV. The foregoing and other advantages of the invention are realized through confirmed delivery of cardiac pacing stimulation to the ventricles. For example, a number of physiologic factors can influence the ability of delivered pacing stimulus to capture a cardiac chamber. For instance, conduction delays through the A-V node and/or the His-Purkinje fibers, electrical conduction delay for sensing intra-cardiac events (from electrodes through threshold sensing circuitry of a medical device), electrical conduction delay for pacing therapy delivery circuitry, electro-mechanical delay associated with the delivery of a pace and the ensuing mechanical contraction, ischemic episodes temporarily tempering conduction pathways, myocardial infarction(s) zones, all can deleteriously impact cardiac conduction and thereby affect an operating pacing therapy delivery regime. Because the conduction status of a patient can vary over time and/or vary based on other factors such as heart rate, autonomic tone and metabolic status, the present invention provides a dynamically controllable resynchronization pacing modality.

According to the invention verification of capture can be triggered so that a desired amount of dual- or single-chamber (fusion-based) CRT delivery ensues. Some of the factors include, (i) completion of a pre-set number of cardiac cycles, (ii) pre-set time limit, (iii) loss of capture of a paced ventricle, (iv) physiologic response triggers (e.g., systemic or intra-cardiac pressure fluctuation, heart rate excursion, metabolic demand increase, decrease in heart wall acceleration, intra-cardiac electrogram morphology or timing, etc.) and/or (v) time of day, and the like. The present invention provides a cardiac pacing system that can readily compensate for the particular implantation sites of the pace/sense electrode pair operatively coupled to a ventricular chamber. When implemented in a triple-chamber embodiment, a pacing system according to the present invention can quickly mode-switch in the event that loss-of-capture (LOC) is declared.

Figure 2:
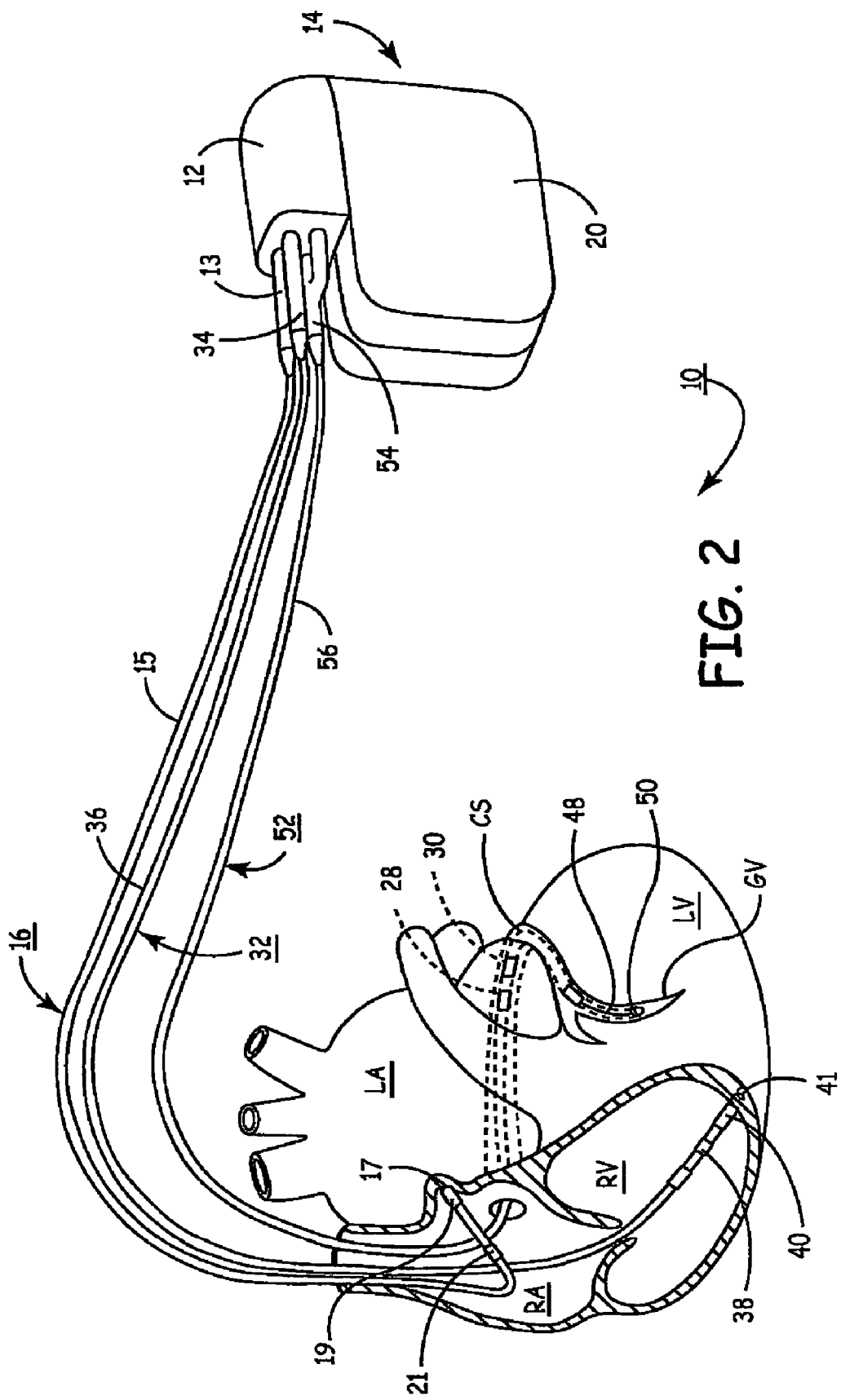
FIG. 2 is a schematic diagram depicting a three channel, atrial and bi-ventricular, pacing system for implementing the present invention.

FIG. 2 is a schematic representation of an implanted, triple-chamber cardiac pacemaker comprising a pacemaker IPG 14 and associated leads 16,32,52 in which the present invention may be practiced. The pacemaker IPG 14 is implanted subcutaneously in a patient's body between the skin and the ribs. The three endocardial leads 16,32,52 operatively couple the IPG 14 with the RA, the RV and the LV, respectively. Each lead has at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions, particularly sensing far field signals (e.g. far field R-waves). The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV. Also, multiple electrodes and/or leads may be deployed into operative communication with a relatively "late" depolarizing ventricle to pace at one or multiple sites with varying degrees of pre-excitation in an effort to produce fusion of an intrinsic depolarization as described in U.S. Pat. No. 6,871,096 to Hill and non-provisional U.S. application Ser. No. 10/803,570 to Mullen and Burnes, the contents of which are incorporated herein. In addition, mechanical and/or metabolic sensors can be deployed independent of, or in tandem with, one or more of the depicted leads. In the event that multiple pacing electrodes are operatively deployed into communication with a single chamber, a capture detection for each such electrode may be individually performed. That is, different pacing stimulus can be implemented for each discrete pacing location and said pacing stimulus delivery can thus be tuned for capture and/or conduction anomalies (e.g., due to infarct or ischemia or the like).

As depicted, a bipolar endocardial RA lead 16 passes through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

Further referring to FIG. 2, a bipolar, endocardial coronary sinus (CS) lead 52 is passed through a vein and the RA chamber of the heart 10, into the coronary sinus and then inferiorly in a branching vessel of the great cardiac vein to extend the proximal and distal LV CS pace/sense electrodes 48 and 50 alongside the LV chamber. The distal end of such a CS lead is advanced through the superior vena cava, the right atrium, the ostium of the coronary sinus, the coronary sinus, and into a coronary vein descending from the coronary sinus, such as the lateral or posteriolateral vein. In addition, while not depicted in FIG. 2 the atrial, ventricular, and/or CS-deployed pacing leads can couple to the exterior of a heart via a pericardial or epicardial attachment mechanism.

In a four chamber or channel embodiment, LV CS lead 52 bears proximal LA CS pace/sense electrodes 28 and 30 positioned along the CS lead body to lie in the larger diameter CS adjacent the LA. Typically, LV CS leads and LA CS leads do not employ any fixation mechanism and instead rely on the close confinement within these vessels to maintain the pace/sense electrode or electrodes at a desired site. The LV CS lead 52 is formed with a multiple conductor lead body 56 coupled at the proximal end connector 54 fitting into a bore of IPG connector block 12. A small diameter lead body 56 is selected in order to lodge the distal LV CS pace/sense electrode 50 deeply in a vein branching from the great vein (GV).

In this case, the CS lead body 56 would encase four electrically insulated lead conductors extending proximally from the more proximal LA CS pace/sense electrode(s) and terminating in a dual bipolar connector 54. The LV CS lead body would be smaller between the LA CS pace/sense electrodes 28 and 30 and the LV CS pace/sense electrodes 48 and 50. It will be understood that LV CS lead 52 could bear a single LA CS pace/sense electrode 28 and/or a single LV CS pace/sense electrode 50 that are paired with the IND_CAN electrode 20 or the ring electrodes 21 and 38, respectively for pacing and sensing in the LA and LV, respectively.

Figure 3:
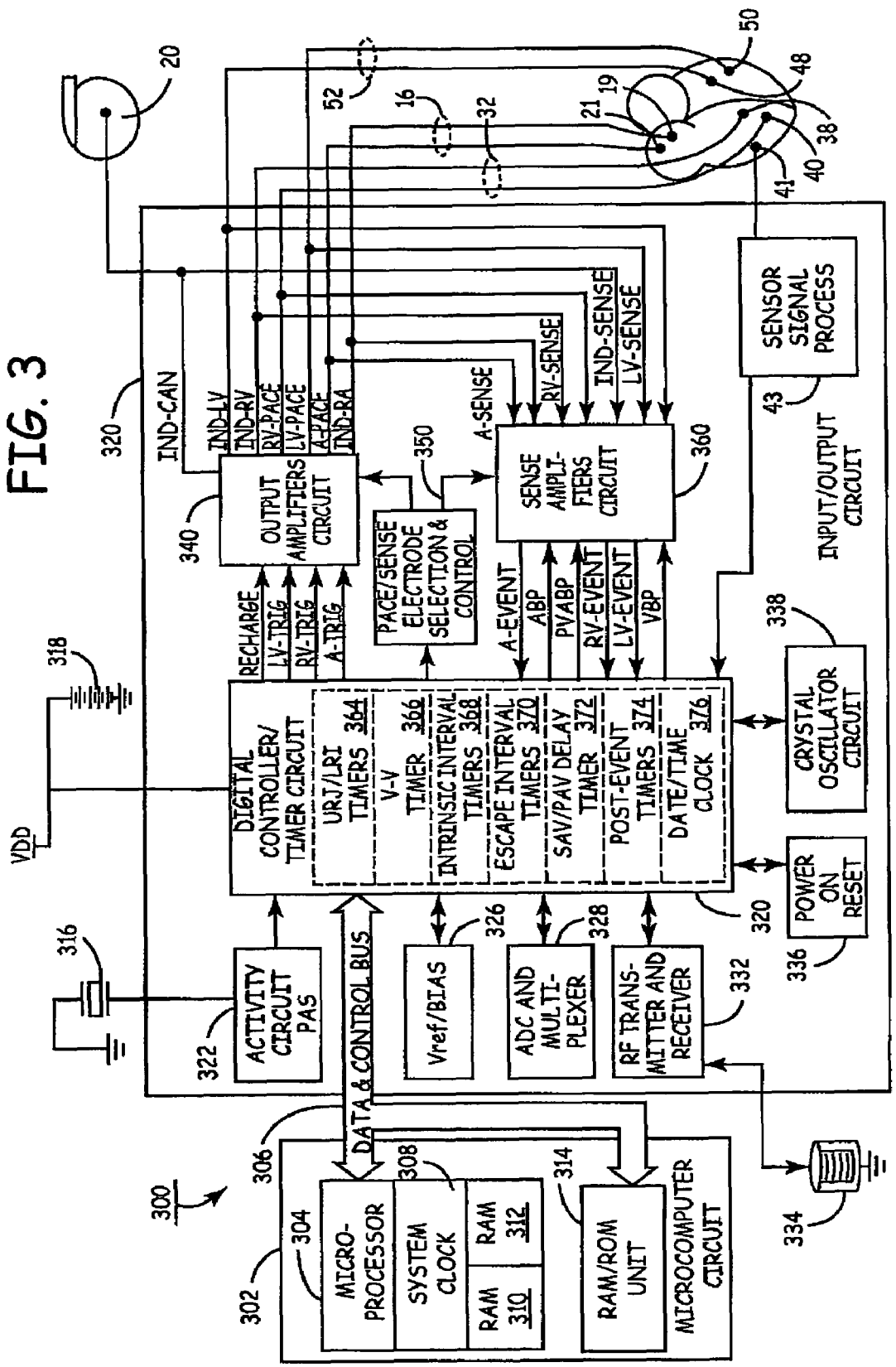
FIG. 3 is a simplified block diagram of one embodiment of IPG circuitry and associated leads employed in the system of FIG. 2 for providing three sensing channels and corresponding pacing channels usable in conjunction with the present invention.

In this regard, FIG. 3 depicts bipolar RA lead 16, bipolar RV lead 32, and bipolar LV CS lead 52 without the LA CS pace/sense electrodes 28 and 30 coupled with an IPG circuit 300 having programmable modes and parameters of a biventricular DDD/R type known in the pacing art. In turn the sensor signal processing circuit 43 indirectly couples to the timing circuit 330 and via bus 306 to microcomputer circuitry 302. The IPG circuit 300 is illustrated in a functional block diagram divided generally into a microcomputer circuit 302 and a pacing circuit 320. The pacing circuit 320 includes the digital controller/timer circuit 330, the output amplifiers circuit 340, the sense amplifiers circuit 360, the RF telemetry transceiver 322, the activity sensor circuit 322 as well as a number of other circuits and components described below.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexer circuit 328 digitizes analog signals and voltage to provide real time telemetry if a cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 322 in the depicted, exemplary IPG circuit 300. The patient activity sensor 316 is coupled to the IPG housing and may take the form of a piezoelectric crystal transducer as is well known in the art and its output signal is processed and used as the RCP. Sensor 316 generates electrical signals in response to sensed physical activity that are processed by activity circuit 322 and provided to digital controller/timer circuit 330. Activity circuit 332 and associated sensor 316 may correspond to the circuitry disclosed in U.S. Pat. Nos. 5,052,388 and 4,428,378. Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Data transmission to and from the external programmer is accomplished by means of the telemetry antenna 334 and an associated RF transceiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 normally operates in a reduced power consumption mode and is interrupt driven. Microprocessor 304 is awakened in response to defined interrupt events, which may include A-TRIG, RV-TRIG, LV-TRIG signals generated by timers in digital timer/controller circuit 330 and A-EVENT, RV-EVENT, and LV-EVENT signals generated by sense amplifiers circuit 360, among others. The specific values of the intervals and delays timed out by digital controller/timer circuit 330 are controlled by the microcomputer circuit 302 by means of data and control bus 306 from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 304 may also serve to define variable, operative AV delay intervals and the energy delivered to each ventricle.

In one embodiment of the invention, microprocessor 304 is a custom microprocessor adapted to fetch and execute instructions stored in RAM/ROM unit 314 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 304.

Digital controller/timer circuit 330 operates under the general control of the microcomputer 302 to control timing and other functions within the pacing circuit 320 and includes a set of timing and associated logic circuits of which certain ones pertinent to the present invention are depicted. The depicted timing circuits include URI/LRI timers 364, V-V delay timer 366, intrinsic interval timers 368 for timing elapsed V-EVENT to V-EVENT intervals or V-EVENT to A-EVENT intervals or the V-V conduction interval, escape interval timers 370 for timing A-A, V-A, and/or V-V pacing escape intervals, an AV delay interval timer 372 for timing the A-LVp delay (or A-RVP delay) from a preceding A-EVENT or A-TRIG, a post-ventricular timer 374 for timing post-ventricular time periods, and a date/time clock 376.

According to the invention, the AV delay interval timer 372 is loaded with an appropriate delay interval for one ventricular chamber (i.e., either an A-RVp delay or an A-LVp delay to time-out starting from a preceding A-PACE or A-EVENT. The interval timer 372 triggers pacing stimulus delivery, and can based on one or more prior cardiac cycles (or from a data set empirically derived for a given patient)

The post-event timers 374 time out the post-ventricular time periods following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 302. The post-ventricular time periods include the PVARP, a post-atrial ventricular blanking period (PAVBP), a ventricular blanking period (VBP), and a ventricular refractory period (VRP). The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 304 also optionally calculates AV delays, post-ventricular time periods, and post-atrial time periods that vary with the sensor based escape interval established in response to the RCP(s) and/or with the intrinsic atrial rate.

The output amplifiers circuit 340 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 330 generates the RV-TRIG signal at the time-out of the A-RVP delay (in the case of RV pre-excitation) or the LV-TRIG at the time-out of the A-LVp delay (in the case of LV pre-excitation) provided by AV delay interval timer 372 (or the V-V delay timer 366). Similarly, digital controller/timer circuit 330 generates an RA-TRIG signal that triggers output of an RA-PACE pulse (or an LA-TRIG signal that triggers output of an LA-PACE pulse, if provided) at the end of the V-A escape interval timed by escape interval timers 370.

The output amplifiers circuit 340 includes switching circuits for coupling selected pace electrode pairs from among the lead conductors and the IND_CAN electrode 20 to the RA pace pulse generator (and LA pace pulse generator if provided), RV pace pulse generator and LV pace pulse generator. Pace/sense electrode pair selection and control circuit 350 selects lead conductors and associated pace electrode pairs to be coupled with the atrial and ventricular output amplifiers within output amplifiers circuit 340 for accomplishing RA, LA, RV and LV pacing.

The sense amplifiers circuit 360 contains sense amplifiers corresponding to any of those presently employed in contemporary cardiac pacemakers for atrial and ventricular pacing and sensing. As noted in the above-referenced, commonly assigned, '324 patent, it has been common in the prior art to use very high impedance P-wave and R-wave sense amplifiers to amplify the voltage difference signal which is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 330 controls sensitivity settings of the atrial and ventricular sense amplifiers 360.

The sense amplifiers are typically uncoupled from the sense electrodes during the blanking periods before, during, and after delivery of a pace pulse to any of the pace electrodes of the pacing system to avoid saturation of the sense amplifiers. The sense amplifiers circuit 360 includes blanking circuits for uncoupling the selected pairs of the lead conductors and the IND_CAN electrode 20 from the inputs of the RA sense amplifier (and LA sense amplifier if provided), RV sense amplifier and LV sense amplifier during the ABP, PVABP and VBP. The sense amplifiers circuit 360 also includes switching circuits for coupling selected sense electrode lead conductors and the IND_CAN electrode 20 to the RA sense amplifier (and LA sense amplifier if provided), RV sense amplifier and LV sense amplifier. Again, sense electrode selection and control circuit 350 selects conductors and associated sense electrode pairs to be coupled with the atrial and ventricular sense amplifiers within the output amplifiers circuit 340 and sense amplifiers circuit 360 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 330. Similarly, left atrial depolarizations or P-waves in the LA-SENSE signal that are sensed by the LA sense amplifier, if provided, result in a LA-EVENT signal that is communicated to the digital controller/timer circuit 330. Ventricular depolarizations or R-waves in the RV-SENSE signal are sensed by a ventricular sense amplifier result in an RV-EVENT signal that is communicated to the digital controller/timer circuit 330. Similarly, ventricular depolarizations or R-waves in the LV-SENSE signal are sensed by a ventricular sense amplifier result in an LV-EVENT signal that is communicated to the digital controller/timer circuit 330. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

To simplify the description herein, it will be assumed that the following references to an "A-EVENT" and "A-PACE" will denote right atrial activity. In the event that the left atrium is monitored (or stimulated), the reader should appreciate that the LA is referred to.

An operating mode 400 of IPG circuit 300 according to the present invention are depicted in the flow chart and described as follows. At decision step 402 a nominal ventricular capture test initiation trigger is implemented. Although as depicted the decision relates to a time of day (i.e., 3:00 a.m.) decision step 402 can include any of a wide variety of temporal or event-based triggers. If the criteria at step 402 is not met then the process continues to step 404 and no action is taken. If the decision is affirmative at step 402 then decision step 406 is implemented wherein any of a variety of criteria for not proceeding with the conduction test 400 are analyzed. If the designated criteria are met then the test 400 does not proceed (at step 408). Representative criteria includes the presence of an arrhythmia, high heart rate, high activity sensor signal input, and the like. If the designated criteria is met then the test 400 proceeds (at step 410) by programming a relatively long A-V delay interval so that the patient's PR interval (i.e., A-event to ventricular depolarization) emerges. The measured PR interval is stored in a computer memory or the like.

Then at step 412 the pacing therapy mode-switches to (or implements) a single ventricular pacing therapy with a relatively short (or minimum) A-V delay interval for at least one cardiac cycle. Then at step 414 if no ventricular sense event (R-sense) occurs in the non-paced ventricle prior to a next-scheduled pacing stimulus delivery, then the method 400 proceeds to step 416 wherein the result of step 414 is evaluated to see if a similar event had occurred in the recent past (e.g., on a given day, within a temporal window, more than once, etc.) which if positive the method 400 returns to step 412. If the lack of an V-sense event is not the first occurrence in a given day, for example, then the method 400 proceed to step 424 wherein the pacing therapy delivery is labeled as loss-of-capture (LOC) before proceeding to step 434, ending the method 400 until a later iteration occurs.

Following a positive result from decision step 414 the method 400 proceeds to decision step 418 wherein the temporal location of the R-sense event is evaluated whether or not it occurred within a short time of the patient's PR interval (e.g., within about 40 ms less than the PR measured interval) is considered. In the event that the V-sense event occurs within a physiologically short period of time before the expiration of the patient's PR interval then at step 420 the V-sensed event is queried whether it was the first such event in the recent past (e.g., on a given day, etc.) and if answered in the affirmative then the method 400 returns to step 412—as described herein. If not, then the pacing regimen is declared as pacing "capture verified" (or equivalent) at step 432.

However, in the that the V-sense event occurs outside the physiologically short period of time before the expiration of the patient's PR interval then the method 400 proceeds to step 422 the V-sensed event is queried whether it was the first such event in the recent past (e.g., on a given day, etc.) and if answered in the affirmative then the method 400 proceeds to step 426 where the R-sense event is compared to a typical physiologic ventricular depolarization following an A-event (e.g., did the V-sense event register at a moment greater than about 310 ms following the A-event. If step 426 is answered in the affirmative then a pacing regimen LOC is declared at step 428 and the method 400 ends at step 434. If step 426 is answered in the negative then the pacing regimen is classified as likely not valid (e.g., "capture suspect" or equivalent) and an optional message logged (at step 430) that the patient's, or device, history merits review and then the method 400 ends at step 434 until the method is later invoked to verify whether ventricular pacing stimuli captures as intended.

The particular operating mode of the present invention is a programmed or hard-wired sub-set of possible CRT delivery operating modes, including bi-ventricular pacing whether involving simultaneous V-V pacing stimulation (i.e., synchronized ventricular pacing therapy delivery) or offset V-V pacing stimulation (e.g., in an attempt to compensate for various cardiac conduction and/or contractile defects). In addition, the invention can be used to verify pacing capture of either one of an RV or an LV (and RA and LA). As noted, the inventive algorithm advantageously helps confirm the capture status of a pacing regimen by providing one of: a LOC signal, a capture signal, or a "capture suspect" signal. Of course, the methods according to the present invention are intended to be stored as executable instructions on any appropriate computer readable medium that provides control signals to effect the technical result of the invention herein described and depicted, although certain of the steps of the inventive methods may be performed manually as well.

Figure 4:
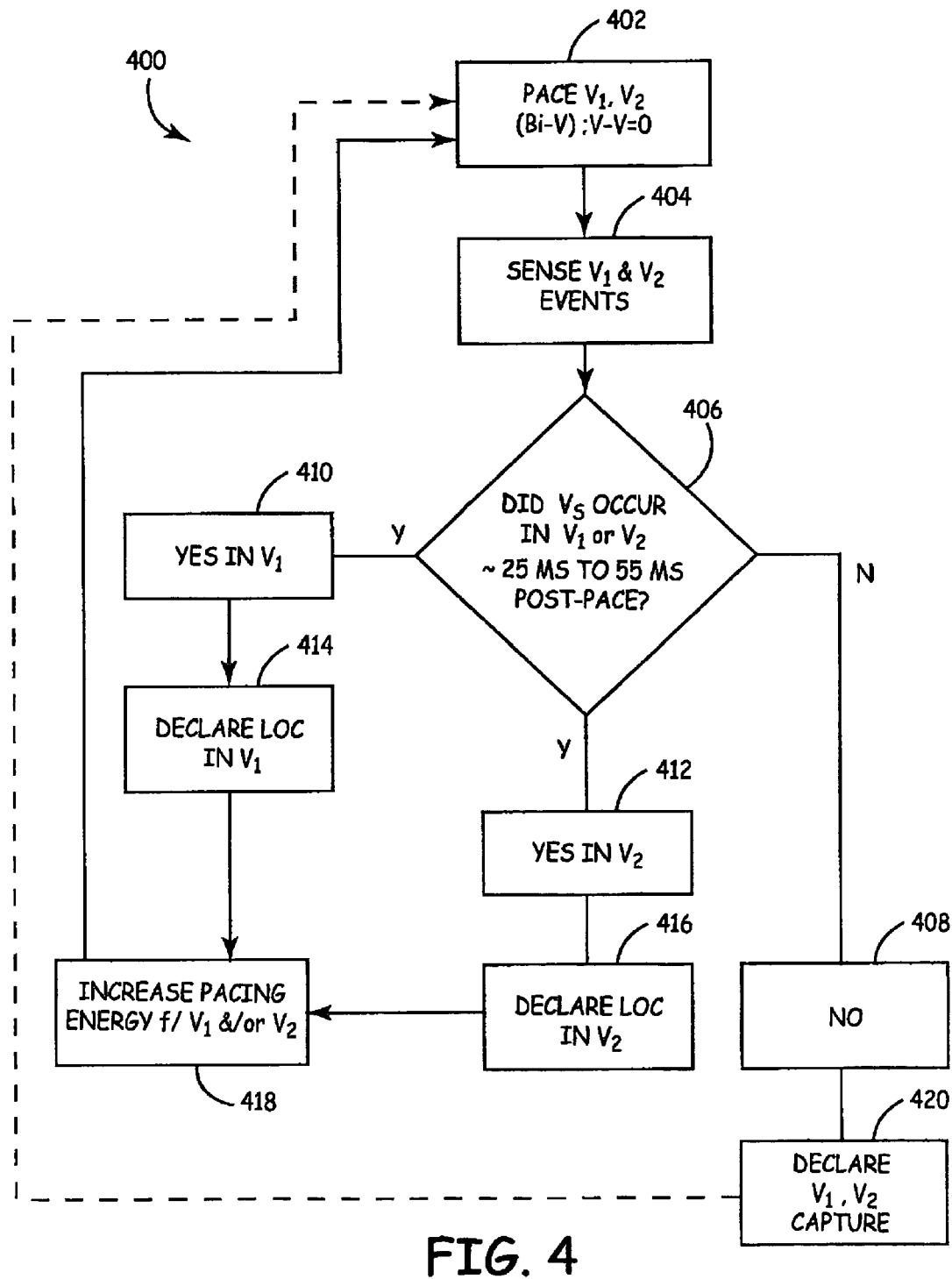
FIG. 4 illustrates an embodiment of the continuous ventricular capture verification according to the present invention.

Referring now to FIG. 4, one embodiment of the invention is depicted in a flow chart as method 400. Beginning at step 402 bi-ventricular pacing therapy delivery to both ventricles occurs, with a nominal zero V-V offset (i.e., not sequential CRT delivery). Then the ventricles are monitored at step 404 to determine if the pacing therapy delivery captured one or both ventricles. At decision step 406 the ventricular sense events (Vs) are compared to determine if the Vs occurred within a window of time too long to identify direct evoked activation but which can be positively identified as inter-ventricular conduction (e.g., beginning at about 25 ms to about 55 ms). If the Vs event in each ventricle lies outside of this window then (at step 408) then the pacing stimulus is declared to be capturing the ventricle (at step 420). However, if at step 410 one ventricle (V1) produced a sensed event in the "inter-ventricular conduction-sensing window" then at 414 the V1 chamber is declared LOC. Then, optionally, at step 418 the pacing energy delivered can be increased and method 400 resumed at step 402. Likewise, if the V2 chamber detects activation during the inter-ventricular conduction-sensing window then the V2 chamber is declared to be LOC (and the optional step 418 performed to return to step 402 at a different energy level).

While depicted in FIG. 4 as a single cycle bi-ventricular capture verification test one ventricle can be tested at a time according to the invention. Also, the inter-ventricular conduction-sensing window can vary depending on a patient's physiology and present status (vis-à-vis activity, stress, drug regimen, etc.) and a given patient's LOC window can be identified acutely with any correlating parameters (e.g., in a look up table correlating heart rate, activity, etc. to the inter-ventricular conduction-sensing window).

In the presently described and depicted embodiment of the invention capture verification testing occurs on a beat-by-beat basis, however, the testing may occur based on a triggering signal (e.g., from a patient or clinician, from a hand-held programmer or the like locally or remotely spaced from said patient) or at a less frequent interval. Upon confirmation of capture of a cardiac chamber, a desired pacing therapy delivery can be re-enabled and continue until: a loss of capture occurs, a predetermined period of time elapses, a mode-switch occurs to another pacing regimen (e.g., due to a automated physiologic trigger, a programming change, etc.) or the like. If a loss of capture in a ventricular chamber is detected it could indicate one or more possible problems requiring remedial action. For example, the pacing electrodes might have malfunctioned or become dislodged, an elongated conductor within a medical electrical lead might have been damaged, open- or short-circuited. Accordingly, in addition to verifying pacing capture, the present invention optionally includes capability for alerting a physician, clinician, patient, health care provider or the like that pacing system interrogation might be required. In addition, the configuration of the pacing system, including collected patient data and physiologic parameters can be stored for later retrieval thereby enhancing the likelihood of an accurate assessment of the operating condition of the pacing system.

In one form of the invention, following detection of inappropriate or non-programmed operating conditions (e.g., including receipt of a LOC signal during CRT delivery) the pacing therapy can be adjusted, discontinued or a mode switch performed to another pacing modality which, for example might exclude the pacing lead that produced the LOC signal. One aspect of this form of the invention, upon receipt of a ventricular LOC signal an intended bi-ventricular or uni-ventricular CRT delivery regimen is suspended and an atrial-pacing only therapy is implemented (e.g., an AAI, ADI, AAI/R, ADI/R and the like). That is, assuming that a patient's A-V conduction remains relatively intact until such time as the patient is able to receive qualified medical attention or until a subsequent ventricular capture verification test indicates that non-suspect capture has been achieved. In this regard, U.S. Pat. No. 6,772,005 to Casavant et al. entitled "Preferred ADI/R: a Permanent Pacing Mode to Eliminate Ventricular Pacing While Maintaining Backup Support" which is assigned to Medtronic, Inc. is hereby incorporated herein by reference in its entirety.

In a yet another related embodiment of the foregoing aspect of the invention, in the event that a ventricular LOC signal persists a mode-switch from a bi-ventricular CRT to a uni-ventricular, fusion-based CRT can occur. In particular if the LOC signal relates to a heart failure patient's first-to-depolarize ventricle such a uni-ventricular, fusion-based CRT delivery regimen characterized by pre-excitation of the second-to-depolarize ventricle can be chronically implemented. In this regard pending non-provisional U.S. patent application Ser. No. 10/803,570 filed 17 Mar. 2004 by J. Burnes and T. Mullen and entitled "APPARATUS AND METHODS OF ENERGY EFFICIENT, ATRIAL-BASED BI-VENTRICULAR FUSION-PACING" is hereby incorporated herein by reference in its entirety.

The patient may, in the best scenario, be relieved of pacing therapy delivery altogether (programming the pacing circuitry to an ODO monitoring-only "pacing modality"). Assuming the patient is not chronotropically incompetent, normal sinus rhythm may emerge permanently for all the activities of daily living. Additionally, the process 600 may be employed to search for a change in conduction status (e.g., wherein a later-to-depolarize ventricle changes from the LV to the RV).

It should be understood that, certain of the above-described structures, functions and operations of the pacing systems of the illustrated embodiments are not necessary to practice the present invention and are included in the description simply for completeness of an exemplary embodiment or embodiments. It will also be understood that there may be other structures, functions and operations ancillary to the typical operation of an implantable pulse generator that are not disclosed and are not necessary to the practice of the present invention.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

The invention claimed is:

1. A method of bi-ventricular pacing therapy, comprising:
   delivering at least one pacing stimulus to a first ventricle via a least one pace/sense electrode disposed in electrical communication with said first ventricle;
   delivering at least one pacing stimulus to a second ventricle via a least one pace/sense electrode disposed in electrical communication with said second ventricle;
   wherein the pacing stimuli are delivered at approximately the same time; and
   in the event that a depolarization wavefront of the first ventricle is sensed in a first interval extending to between about 25 ms and about 55 ms after delivery of the pacing stimulus to the first ventricle, declaring capture of said first ventricle;
   in the event that a depolarization wavefront is detected by the pace/sense electrode of the first ventricle within a second interval following the first interval, following pacing delivery, then declaring loss-of-capture (LOC) of said first ventricle; and
   in the event that a depolarization wavefront is detected by the pace/sense electrodes of the second ventricle within a second interval following the first interval, following pacing delivery, then declaring loss-of-capture (LOC) of said second ventricle.

2. A method according to claim 1, further comprising: filtering signals related to sensed depolarization wavefronts.

3. A method according to claim 2, wherein the filtering of signals related to sensed depolarization wavefronts comprises applying to the signals at least one of: a band-pass filtering step, a high-pass filtering step, a low-pass filtering step, imposing a temporal blanking period.

4. A method according to claim 1, wherein the bi-ventricular pacing therapy comprises a cardiac resynchronization therapy.

5. A method according to claim 4, wherein the cardiac resynchronization therapy further comprises a fusion-based cardiac resynchronization therapy.

6. A method according to claim 1, wherein the method is performed periodically.

7. A method according to claim 1, wherein the method is performed for a single cardiac cycle.

8. A method according to claim 1, wherein the method is performed substantially continuously.

9. A method according to claim 1, further comprising: upon receiving the declaration of LOC, for at one subsequent cardiac cycle, repeating the claimed method.

10. A method according to claim 1, further comprising: responsive to the declaration of LOC, for at least one subsequent cardiac cycle, storing or measuring at least one of the following operative pacing parameters:
    a pacing stimulus pulse width,
    a pacing stimulus amplitude,
    a pacing stimulus polarity,
    a pacing stimulus frequency.

11. A method according to claim 1, further comprising: responsive to the declaration of LOC, for at least one subsequent cardiac cycle, storing or measuring at least one of the following pacing parameters:
    a pacing rate signal,
    a cardiac pressure output signal,
    a minute ventilation output signal,
    an activity sensor output signal,
    an acceleration output signal,
    a pulmonary edema parameter,
    a myocardial ischemia parameter.

12. A method according to claim 1, wherein the first ventricle consists of a left ventricular (LV) chamber and the pace/sense electrode disposed in electrical communication with said first ventricle is disposed in a portion of one of:
    a coronary sinus,
    a portion of a great vein,
    a portion of a vessel branching from the great vein.

13. A method according to claim 12, wherein one of the at least one pacing pulses is delivered between:
    a tip and a ring pacing electrode, a pair of electrodes, a coil and a can-based electrode, a pair of coil electrodes, an epicardial electrode and a second electrode, or a subcutaneous electrode and the second electrode.

* * * * *